(12) United States Patent
Ivri

(10) Patent No.: US 12,295,881 B2
(45) Date of Patent: May 13, 2025

(54) TOPICAL OCULAR DELIVERY DEVICES AND METHODS FOR USING THE SAME

(71) Applicant: Bausch + Lomb Ireland Limited, Dublin (IE)

(72) Inventor: Yehuda Ivri, Newport Coast, CA (US)

(73) Assignee: Bausch + Lomb Ireland Limited, Dublin (IE)

( * ) Notice: Subject to any disclaimer, the term of this patent is extended or adjusted under 35 U.S.C. 154(b) by 0 days.

(21) Appl. No.: 16/972,085

(22) PCT Filed: Jul. 2, 2019

(86) PCT No.: PCT/US2019/040354
§ 371 (c)(1),
(2) Date: Dec. 4, 2020

(87) PCT Pub. No.: WO2020/010116
PCT Pub. Date: Jan. 9, 2020

(65) Prior Publication Data
US 2021/0220169 A1   Jul. 22, 2021

Related U.S. Application Data

(60) Provisional application No. 62/693,818, filed on Jul. 3, 2018.

(51) Int. Cl.
*A61F 9/00* (2006.01)
(52) U.S. Cl.
CPC .................................. *A61F 9/0008* (2013.01)

(58) Field of Classification Search
CPC ... A61F 9/0008; B05B 1/083; B05B 17/0661; B05B 17/0638; B05B 17/0607;
(Continued)

(56) References Cited

U.S. PATENT DOCUMENTS 3,640,274 A     2/1972  Costello
3,779,245 A  *  12/1973  Windsor ............... A61F 9/0008
                                                  604/300

(Continued)

FOREIGN PATENT DOCUMENTS

CN        103118642 A      5/2013
CN        104146816 A     11/2014
(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.

(Continued)

*Primary Examiner* — Jessica Arble
*Assistant Examiner* — Hans Kaliher
(74) *Attorney, Agent, or Firm* — Perilla Knox & Hildebrandt LLP; Stephanie L. Davy-Jow

(57) ABSTRACT

Topical ocular delivery devices are provided. Aspects of the devices include a transducer configured to oscillate at an amplitude and frequency that provides for an emitted stream velocity which results in minimal discomfort during topical ocular delivery. Also provided are methods of using the devices, e.g., in topical ocular delivery applications.

16 Claims, 4 Drawing Sheets

(58) Field of Classification Search
CPC .. A61M 11/005; A61M 11/00; A61M 11/001; A61M 15/0085
See application file for complete search history.

(56) References Cited

U.S. PATENT DOCUMENTS

| | | |
|---|---|---|
| 3,812,854 A | 5/1974 | Michaels et al. |
| 3,861,386 A | 1/1975 | Harris |
| 3,934,585 A | 1/1976 | Maurice |
| 3,970,250 A | 7/1976 | Drews |
| 3,976,072 A | 8/1976 | Walker |
| 4,159,803 A | 7/1979 | Cameto |
| 4,300,546 A | 11/1981 | Kruber |
| 4,334,531 A | 6/1982 | Reichl |
| 4,338,576 A | 7/1982 | Takahashi et al. |
| 4,344,744 A | 8/1982 | Schuster et al. |
| 4,352,459 A | 10/1982 | Berger |
| 4,465,234 A | 8/1984 | Maehara |
| 4,632,311 A | 12/1986 | Nakane |
| 4,655,393 A | 4/1987 | Berger |
| 4,793,339 A | 12/1988 | Matsumoto et al. |
| 4,850,534 A | 7/1989 | Takahashi |
| 4,882,150 A | 11/1989 | Kaufman |
| 4,952,581 A | 8/1990 | Bito |
| 4,961,345 A | 10/1990 | Tsuruoka |
| 4,976,259 A | 12/1990 | Higson |
| 4,981,625 A | 1/1991 | Rhim |
| 5,025,957 A | 6/1991 | Ranalletta |
| 5,171,306 A | 12/1992 | Vo |
| 5,232,363 A | 8/1993 | Meller |
| 5,368,582 A | 11/1994 | Bertera |
| 5,370,317 A | 12/1994 | Weston |
| 5,487,378 A | 1/1996 | Robertson |
| 5,549,249 A | 8/1996 | Foster |
| 5,624,057 A | 4/1997 | Lifshey |
| 5,627,611 A | 5/1997 | Scheiner |
| 5,630,793 A * | 5/1997 | Rowe .................. A61F 9/0008 604/289 |
| 5,657,926 A | 8/1997 | Toda |
| 5,692,651 A | 12/1997 | Fuchs |
| 5,811,443 A | 9/1998 | DeSantis, Jr. |
| 5,828,394 A | 10/1998 | Khuri-Yakub et al. |
| 5,938,117 A | 8/1999 | Ivri |
| 5,958,342 A | 9/1999 | Gamble |
| 5,960,224 A | 9/1999 | Sanada et al. |
| 6,024,717 A * | 2/2000 | Ball .................. A61M 37/0092 604/500 |
| 6,062,212 A | 5/2000 | Davison |
| 6,065,623 A | 5/2000 | Hierzer |
| 6,095,376 A | 8/2000 | Hennemann |
| 6,196,218 B1 | 3/2001 | Voges |
| 6,232,129 B1 | 5/2001 | Wiktor |
| 6,273,092 B1 | 8/2001 | Nolan |
| 6,302,101 B1 | 10/2001 | Py |
| 6,467,476 B1 | 10/2002 | Ivri |
| RE38,077 E | 4/2003 | Cohen |
| 6,543,442 B2 | 4/2003 | Gonda |
| 6,629,646 B1 | 10/2003 | Ivri |
| 6,730,066 B1 | 5/2004 | Bennwik |
| 6,758,837 B2 | 7/2004 | Peclat |
| 6,869,275 B2 | 3/2005 | Dante et al. |
| 7,066,398 B2 | 6/2006 | Borland |
| 7,105,357 B1 | 9/2006 | Kalkum |
| 7,201,732 B2 | 4/2007 | Anderson |
| 7,314,938 B2 | 1/2008 | Shen |
| 7,571,722 B2 | 8/2009 | Wuttke |
| 7,745,460 B2 | 6/2010 | Shen |
| 7,790,743 B2 | 9/2010 | Shen |
| 7,874,467 B2 | 1/2011 | Pardes |
| 7,883,031 B2 | 2/2011 | Collins, Jr. |
| 7,928,122 B2 | 4/2011 | Shen |
| 8,012,136 B2 | 9/2011 | Collins, Jr. |
| 8,048,047 B2 | 11/2011 | Domash |
| 8,056,766 B2 | 11/2011 | Grevin |
| 8,128,606 B2 | 3/2012 | Anderson |
| 8,133,210 B2 | 3/2012 | Al-Abdulla |
| 8,144,399 B2 | 3/2012 | Steenblik |
| 8,168,655 B2 | 5/2012 | Gadek |
| 8,273,307 B2 | 9/2012 | Eickhoff |
| 8,367,701 B2 | 2/2013 | Burnier |
| 8,398,001 B2 | 3/2013 | Borland |
| 8,435,544 B2 | 5/2013 | Mitra |
| 8,544,462 B2 | 10/2013 | Papania |
| 8,545,463 B2 | 10/2013 | Collins, Jr. |
| 8,592,450 B2 | 11/2013 | Gadek |
| 8,629,111 B2 | 1/2014 | Acheampong |
| 8,633,162 B2 | 1/2014 | Acheampong |
| 8,642,556 B2 | 2/2014 | Acheampong |
| 8,648,048 B2 | 2/2014 | Acheampong |
| 8,684,980 B2 | 4/2014 | Hunter |
| 8,685,930 B2 | 4/2014 | Acheampong |
| 8,722,728 B2 | 5/2014 | Wong |
| 8,733,935 B2 | 5/2014 | Ballou, Jr. et al. |
| 8,863,998 B2 | 10/2014 | Painchaud |
| 8,927,574 B2 | 1/2015 | Burnier |
| 8,927,921 B1 | 1/2015 | Nelms |
| 8,936,021 B2 | 1/2015 | Collins, Jr. |
| 9,039,666 B2 | 5/2015 | Voss |
| 9,068,566 B2 | 6/2015 | Ivri |
| 9,085,553 B2 | 7/2015 | Zeller |
| 9,087,145 B2 | 7/2015 | Ballou, Jr. |
| 9,186,690 B2 | 11/2015 | Scanlon |
| 9,216,174 B2 | 12/2015 | Shen |
| 9,238,532 B2 | 1/2016 | Decock |
| 9,248,191 B2 | 2/2016 | Acheampong |
| 9,353,088 B2 | 5/2016 | Burnier |
| 9,447,077 B2 | 9/2016 | Burnier |
| 9,597,230 B2 | 3/2017 | Haffner |
| 9,676,525 B2 | 6/2017 | Greiner-Perth |
| 9,700,686 B2 | 7/2017 | Gavini |
| 9,801,757 B2 | 10/2017 | Voss |
| 9,808,825 B2 | 11/2017 | Aguilar |
| 9,867,933 B2 | 1/2018 | Pardes |
| 9,890,141 B2 | 2/2018 | Burnier |
| 10,073,949 B2 | 9/2018 | Ballou, Jr. |
| 10,105,720 B2 | 10/2018 | Decock |
| 10,124,000 B2 | 11/2018 | Shen |
| 10,154,923 B2 | 12/2018 | Hunter |
| 10,174,017 B2 | 1/2019 | deLong |
| 10,314,740 B2 | 6/2019 | Kraft |
| 10,624,781 B2 | 4/2020 | Ivri |
| 11,278,448 B2 | 3/2022 | Palanker |
| 2001/0035184 A1 | 11/2001 | Schuler et al. |
| 2001/0036424 A1 | 11/2001 | Takahashi |
| 2001/0036449 A1 | 11/2001 | Garst |
| 2002/0078947 A1 | 6/2002 | Gumaste |
| 2002/0124843 A1 | 9/2002 | Skiba |
| 2002/0158196 A1 | 10/2002 | Berggren |
| 2002/0161344 A1 | 10/2002 | Peclat |
| 2002/0185125 A1 | 12/2002 | Klimowicz |
| 2002/0190079 A1 | 12/2002 | Hamamoto |
| 2003/0052573 A1 | 3/2003 | Wischnewskiy |
| 2003/0065294 A1 | 4/2003 | Pickup |
| 2003/0071071 A1 | 4/2003 | Garcia |
| 2003/0140921 A1 | 7/2003 | Smith |
| 2004/0039355 A1 | 2/2004 | Gonzalez |
| 2004/0050861 A1 | 3/2004 | Lisec |
| 2004/0138630 A1 | 7/2004 | Al-Abdulla |
| 2004/0163645 A1 | 8/2004 | Connelly |
| 2004/0173642 A1 | 9/2004 | Clifford |
| 2004/0204674 A1 | 10/2004 | Anderson |
| 2004/0215157 A1 | 10/2004 | Peclat |
| 2004/0256487 A1 | 12/2004 | Collins |
| 2004/0263567 A1 | 12/2004 | Hess et al. |
| 2005/0001981 A1 | 1/2005 | Anderson |
| 2005/0006417 A1 | 1/2005 | Nicol |
| 2005/0107832 A1 | 5/2005 | Bernabei |
| 2005/0172962 A1 | 8/2005 | Gumaste |
| 2005/0207917 A1 | 9/2005 | Koerner et al. |
| 2005/0240162 A1 | 10/2005 | Chen |
| 2005/0261641 A1 | 11/2005 | Warchol |
| 2006/0065677 A1 | 3/2006 | Py |
| 2006/0069358 A1 | 3/2006 | Gerondale |
| 2006/0147313 A1 | 7/2006 | Zengerle |

(56) References Cited

U.S. PATENT DOCUMENTS

| | | |
|---|---|---|
| 2006/0210604 A1 | 9/2006 | Dadey et al. |
| 2007/0051362 A1 | 3/2007 | Sullivan |
| 2007/0088267 A1 | 4/2007 | Shekalim |
| 2007/0088268 A1 | 4/2007 | Edwards |
| 2007/0102455 A1 | 5/2007 | Stark |
| 2007/0119969 A1 | 5/2007 | Collins |
| 2007/0195151 A1 | 8/2007 | Anderson |
| 2007/0268340 A1 | 11/2007 | Dacquay |
| 2007/0295332 A1 | 12/2007 | Ziegler et al. |
| 2008/0039807 A1 | 2/2008 | Pine |
| 2008/0202514 A1 | 8/2008 | Kriksunov |
| 2008/0214940 A1 | 9/2008 | Benaron |
| 2008/0233053 A1 | 9/2008 | Gross |
| 2008/0247264 A1 | 10/2008 | Gabl |
| 2008/0257911 A1 | 10/2008 | Choi |
| 2009/0060793 A1 | 3/2009 | Eickhoff |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds |
| 2009/0212133 A1 | 8/2009 | Collins, Jr. |
| 2009/0223513 A1 | 9/2009 | Papania |
| 2010/0001090 A1 | 1/2010 | Neergaard |
| 2010/0005903 A1 | 1/2010 | Beavis |
| 2010/0013352 A1 | 1/2010 | Pletner |
| 2010/0044460 A1 | 2/2010 | Sauzade |
| 2010/0072301 A1 | 3/2010 | Cater |
| 2010/0072302 A1 | 3/2010 | Cater |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. |
| 2010/0295420 A1 | 11/2010 | Wierach |
| 2010/0326431 A1 | 12/2010 | Yu |
| 2011/0074247 A1 | 3/2011 | Hohlfeld |
| 2011/0102735 A1 | 5/2011 | Gupta |
| 2011/0106025 A1 | 5/2011 | Hall |
| 2011/0146670 A1 | 6/2011 | Gallem et al. |
| 2011/0284579 A1 | 11/2011 | Pardes |
| 2011/0293452 A1 | 12/2011 | Kim |
| 2011/0305425 A1 | 12/2011 | Fabrykowski et al. |
| 2012/0017898 A1 | 1/2012 | Moller |
| 2012/0062840 A1 | 3/2012 | Ballou, Jr. |
| 2012/0070467 A1 | 3/2012 | Ballou, Jr. |
| 2012/0143152 A1 | 6/2012 | Hunter |
| 2012/0179122 A1 | 7/2012 | Eilat |
| 2012/0197219 A1 | 8/2012 | Scanlon |
| 2012/0304929 A1* | 12/2012 | Ivri ................ B05B 15/62 |
| | | 118/712 |
| 2013/0002095 A1 | 1/2013 | Van der Linden |
| 2013/0017283 A1 | 1/2013 | Zemel |
| 2013/0025038 A1* | 1/2013 | Frey ................ E03D 9/032 |
| | | 4/222 |
| 2013/0053042 A1 | 2/2013 | Tanikawa |
| 2013/0079733 A1 | 3/2013 | Burt et al. |
| 2013/0118619 A1 | 5/2013 | Loth |
| 2013/0140225 A1 | 6/2013 | Decock |
| 2013/0150812 A1 | 6/2013 | Hunter |
| 2013/0152796 A1 | 6/2013 | Pawl |
| 2013/0153677 A1 | 6/2013 | Leen |
| 2013/0164436 A1 | 6/2013 | Yagi et al. |
| 2013/0172830 A1 | 7/2013 | Hunter |
| 2013/0206857 A1 | 8/2013 | Ivri |
| 2013/0299607 A1 | 11/2013 | Wilkerson |
| 2013/0345672 A1 | 12/2013 | Ferreri |
| 2014/0088524 A1 | 3/2014 | Marx |
| 2014/0113946 A1 | 4/2014 | Abad |
| 2014/0157956 A1 | 6/2014 | Date |
| 2014/0171490 A1 | 6/2014 | Gross |
| 2014/0187969 A1* | 7/2014 | Hunter ................ A61B 3/14 |
| | | 604/521 |
| 2014/0214024 A1 | 7/2014 | Eichler |
| 2014/0224267 A1 | 8/2014 | Levitz |
| 2014/0242022 A1 | 8/2014 | Vehige |
| 2014/0249491 A1 | 9/2014 | Ballou, Jr. |
| 2014/0257172 A1 | 9/2014 | Yalamanchili |
| 2014/0274910 A1 | 9/2014 | Cumberlidge |
| 2014/0276054 A1 | 9/2014 | Hossack |
| 2014/0285121 A1 | 9/2014 | Balogh |
| 2014/0323931 A1 | 10/2014 | Avni |
| 2014/0336596 A1 | 11/2014 | Wochele |
| 2014/0336618 A1 | 11/2014 | Wilkerson |
| 2015/0018781 A1 | 1/2015 | Rinderknect |
| 2015/0035180 A1 | 2/2015 | Shen |
| 2015/0036219 A1 | 2/2015 | Shen |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld |
| 2015/0144128 A1 | 5/2015 | Hijlkema |
| 2015/0209174 A1 | 7/2015 | Abreu |
| 2015/0209178 A1 | 7/2015 | Blakey |
| 2015/0238689 A1 | 8/2015 | Shimizu |
| 2015/0256730 A1 | 9/2015 | Shen |
| 2015/0276994 A1 | 10/2015 | Shen |
| 2015/0308421 A1 | 10/2015 | Vogt |
| 2015/0328151 A1 | 11/2015 | Ballou, Jr. |
| 2015/0352297 A1 | 12/2015 | Stedman |
| 2016/0107180 A1 | 4/2016 | Decock |
| 2016/0120833 A1 | 5/2016 | Wan |
| 2016/0129467 A1 | 5/2016 | Ciardella |
| 2016/0199225 A1 | 7/2016 | Ivri |
| 2016/0199230 A1 | 7/2016 | Doshi |
| 2016/0213866 A1 | 7/2016 | Tan |
| 2016/0263314 A1 | 9/2016 | Pardes |
| 2016/0296367 A1* | 10/2016 | Ivri ................ A61F 9/0008 |
| 2016/0354559 A1* | 12/2016 | Gavini ................ A61K 31/546 |
| 2017/0028626 A1 | 2/2017 | Delrot |
| 2017/0136484 A1 | 5/2017 | Wilkerson |
| 2017/0138357 A1 | 5/2017 | Kondo et al. |
| 2017/0151088 A1 | 6/2017 | Ballou, Jr. |
| 2017/0156927 A1 | 6/2017 | Richter |
| 2017/0182510 A1 | 6/2017 | Wilkerson |
| 2017/0187969 A1 | 6/2017 | Kitamori |
| 2017/0274159 A1 | 9/2017 | Gavini |
| 2017/0344714 A1 | 11/2017 | Ballou, Jr. |
| 2018/0085251 A1 | 3/2018 | Hunter |
| 2018/0108275 A1 | 4/2018 | Newberry |
| 2018/0116871 A1 | 5/2018 | Hunter |
| 2018/0207030 A1 | 7/2018 | Ivri |
| 2018/0229247 A1 | 8/2018 | Laidler |
| 2018/0236466 A1 | 8/2018 | Laidler |
| 2018/0297053 A1 | 10/2018 | Buckland |
| 2019/0053945 A1 | 2/2019 | Hunter |
| 2019/0074086 A1 | 3/2019 | Ballou, Jr. |
| 2019/0099071 A1 | 4/2019 | Ehrmann |
| 2019/0314195 A1 | 10/2019 | Ivri |
| 2019/0314196 A1 | 10/2019 | Ivri |
| 2019/0314197 A1 | 10/2019 | Ivri |
| 2019/0314198 A1 | 10/2019 | Ivri |
| 2020/0022416 A1 | 1/2020 | Alarcon |
| 2020/0197218 A1* | 6/2020 | Newell ................ A61F 9/0008 |
| 2020/0197220 A1 | 6/2020 | Ivri |
| 2020/0246182 A1 | 8/2020 | Ivri |
| 2020/0281768 A1 | 9/2020 | Quintana |
| 2020/0315842 A1* | 10/2020 | Palanker ................ A61F 9/0026 |
| 2020/0330267 A1* | 10/2020 | Li ................ A61M 35/00 |
| 2021/0128350 A1 | 5/2021 | Ivri |
| 2021/0137732 A1 | 5/2021 | Quintana |
| 2021/0322209 A1 | 10/2021 | Ivri |
| 2021/0322210 A1 | 10/2021 | Ivri |
| 2022/0039998 A1 | 2/2022 | Ivri |
| 2022/0125631 A1 | 4/2022 | Ianchulev |
| 2022/0160542 A1 | 5/2022 | Palanker |
| 2022/0192874 A1 | 6/2022 | Ivri |

FOREIGN PATENT DOCUMENTS

| | | |
|---|---|---|
| CN | 104582647 A | 4/2015 |
| CN | 204813955 U * | 12/2015 |
| CN | 105351426 A | 2/2016 |
| CN | 107530509 A | 1/2018 |
| EP | 0622035 A1 | 11/1994 |

(56) References Cited

FOREIGN PATENT DOCUMENTS

| | | |
|---|---|---|
| EP | 0622035 B1 | 3/1999 |
| EP | 1493410 A2 | 1/2005 |
| JP | H08251948 A | 9/1996 |
| JP | 3055480 U | 1/1999 |
| JP | 2007531577 A | 11/2007 |
| JP | 2013535250 A | 9/2013 |
| KR | 10-1258025 B1 | 4/2013 |
| KR | 10-2013-0054352 A | 5/2013 |
| WO | 1994020875 A3 | 1/1995 |
| WO | 1996000050 A1 | 1/1996 |
| WO | 2000005482 A1 | 2/2000 |
| WO | 2001046134 A1 | 6/2001 |
| WO | 2002072169 A2 | 9/2002 |
| WO | WO-02072169 A2 * | 9/2002 ........... A61F 9/0008 |
| WO | 2010078428 A1 | 7/2010 |
| WO | 2012009706 A1 | 1/2012 |
| WO | 2013076682 A1 | 5/2013 |
| WO | 2013090459 A1 | 6/2013 |
| WO | 2013090468 A1 | 6/2013 |
| WO | 2013155201 A2 | 10/2013 |
| WO | 2013158967 A3 | 12/2013 |
| WO | 2016115050 A1 | 7/2016 |
| WO | 2016164830 A1 | 10/2016 |
| WO | 2018136618 A2 | 7/2018 |
| WO | 2018227190 A1 | 12/2018 |
| WO | 2019113483 A1 | 6/2019 |
| WO | 2020010116 A1 | 1/2020 |

OTHER PUBLICATIONS

Ali et al., "Glaucoma and Dry Eye", Ophthalmology, 2009, vol. 116, p. 1232.

Birkhoff et al., "New Devices for Dispensing Ophthalmic Treatments May Be the Key to Managing the Life Cycles of Established Products", 2010, Drug Delivery Technology, vol. 10, pp. 16-21.

Brenton, "CRUK/10/30: TRICON8—Sample collection of ovarian cancer tissues and blood for translational research from patients participating in the CR-UK/MRC ICON8 trial", 2015, online abstract.

Choi et al., "Generation of Controllable Monodispersed Sprays Using Impulse Jet and Charging Techniques", Review of Scientific Instruments, 1990, vol. 61, pp. 1689-1693.

Denion et al., "A 5-Minute Interval between Two Dilating Eye Drops Increases Their Effect", Jul. 19, 2017, Optometry and Vision Science, vol. 94, pp. 838-844.

Electronic Tutorials, "Linear Solenoid Actuator", 2016 [online]; [Retrieved on Oct. 17, 2022], Retrieved from the Internet URL: https://www.electronics-tutorials.ws/io/io_6.html.

Elert, Glenn, "Spherical mirrors", The Physics Hypertextbook, 2021 [online]; [Retrieved on Oct. 17, 2022], Retrieved from the Internet URL: https://physics.info/mirrors/.

Gannon, Megan, "The Best Length for Eyelashes, According to Science", Feb. 24, 2015 [online]; [Retrieved on Oct. 17, 2022], Retrieved from the Internet URL: https://www.livescience.com/49934-optimal-length-for-eyelashes-discovered.html.

Ianchulev et al., "Pharmacodynamic profile of mydriatic agents delivered by ocular piezo-ejection microdosing compared with conventional eyedropper", 2016, Ther. Deliv., vol. 7, pp. 751-760.

Jow et al., "Design and Optimization of Printed Spiral Coils for Efficient Transcutaneous Inductive Power Transmission", IEEE Transactions on Biomedical Circuits and Systems, 2007, vol. 1, pp. 193-202.

Kent, Christopher, "Getting Meds onto the Eye, 21st Century Style", Mar. 15, 2013 [online]; [Retrieved on Aug. 27, 2019], Retrieved from the Internet URL: https://www.reviewofophthalmology.com/article/getting-meds-onto-the-eye-21st-century-style.

Kompella et al., "ISOPT Clinical Hot Topic Panel Discussion on Ocular Drug Delivery", 2019, J. Ocul. Pharmacol. Ther., vol. 35, pp. 457-465.

Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.

Lindblad et al., "Production of Uniform-Sized Liquid Droplets", Journal of Scientific Instruments, 1965, vol. 42, pp. 635-638.

Lux et al., "A Comparative Bioavailability Study of Three Conventional Eye Drops Versus a Single Lyophilisate", Br. J. Ophthalmol., 2003, vol. 87, pp. 436-440.

Macmillan Online Dictionary, "Stream," n.d. [online]; [Retrieved on Dec. 13, 2018]; Retrieved from the Internet URL: https://macmillandictionary.com/dictionary/american/stream_ 1#stream_ 9.

Marx et al., "Opthalmic Squeeze Dispenser: Eliminating the Need for Additives in Multidose Preservative-Free Eyecare Formulations", 2017, Drug Development Delivery, vol. 17, pp. 40-44.

Merriam-Webster, "Clamp," 2019 [online]; [Retrieved on Oct. 25, 2022], Retrieved from the Internet URL: https://www.merriam-webster.com/dictionary/clamp.

Merriam-Webster, "Collimate," 2020 [online]; [Retrieved on Oct. 17, 2022], Retrieved from the Internet URL: https://www.merriam-webster.com/dictionary/collimated.

Merriam-Webster, "Stream," n.d. [online]; [Retrieved on Dec. 13, 2018], Retrieved from the Internet URL: https://www.merriam-webster.com/dictionary/stream.

Murube et al., "Classification of Artificial Tears, I: Composition and Properties", Advanced Experimental Medical Biology, 1998, vol. 438, pp. 693-704.

Murube et al., "Classification of Artificial Tears, II: Additives and Commercial Formulas", Advanced Experimental Medical Biology, 1998, vol. 438, pp. 705-715.

Oxford Online Dictionary, "Stream," n.d. [online]; [Retrieved on Dec. 13, 2018]; Retrieved from the Internet URL: https://en.oxforddictionaries.com/definition/us/stream.

Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

Vocabulary.com, "Stream," n.d. [online]; [Retrieved on Dec. 13, 2018]; Retrieved from the Internet URL: https://www.dictionary.com/stream.

International Search Report and Written Opinion dated Sep. 24, 2019 in corresponding International Patent Application No. PCT/US2019/040354 (8 pages).

* cited by examiner

TOPICAL OCULAR DELIVERY DEVICES AND METHODS FOR USING THE SAME

CROSS-REFERENCE TO RELATED APPLICATIONS

This application is a U.S. National Stage Application of PCT Application Serial Number PCT/US2019/040354 filed on Jul. 2, 2019, which application pursuant to 35 U.S.C. § 119(e), claims priority to the filing date of U.S. Provisional Patent Application Ser. No. 62/693,818 filed Jul. 3, 2018; the disclosure of which application is herein incorporated by reference.

INTRODUCTION

There are many situations in which it is desirable to administer a liquid formulation to an ocular surface, e.g., for the treatment of an ocular condition, such as a disease condition, for the alleviation of discomfort, e.g., dry eye, for the improvement of appearance, e.g., bloodshot eye, and for diagnostic purposes. The administration of liquid formulations onto an ocular surface generally is accomplished by depositing one or more drops of the liquid formulation from a small container or bottle (e.g., a conventional eye dropper) directly onto the ocular surface. In such instances, the drops of the liquid formulation are either self-administered or administered by another, such as a health care provider or caregiver.

A conventional eye dropper dispenses single drops that are about 30-50 µl in volume. However, since the human eye can typically retain only about 7 µl of fluid on the corneal surface, larger deposited volumes result in overflow and loss of most of the medication from the eye surface. In addition, a large volume of a single drop, such as 30 or 50 µl, causes a blinking reflex, which removes the majority of the fluid from the ocular surface, and also causes discomfort and reflex tearing.

These factors can make administration of eye drops from conventional eye droppers (whether self-administered or administered by another) problematic. For example, with conventional eye droppers it is not possible to administer a precise, known dose of a liquid formulation and active agent to the eye. Furthermore, there is substantial waste that occurs using conventional eye droppers. In addition, administration by conventional eye dropper can result in patient discomfort.

Many types of ultrasonic fluid ejection devices have been developed for atomizing and dispensing of liquids. These atomizers utilize an enclosed chamber, which further includes a perforated membrane or a pinhole membrane as the front wall of the chamber and further includes a means to vibrate the membrane, typically by a piezoelectric transducer affixed to the edge of the membrane. As a result, acoustic pressure waves are generated in the liquid forcing fluid droplets through the open pinholes. Such devices have been described in the following publications: United States Published Patent Application Publication No. 2014/0187969 and U.S. Pat. Nos. 3,812,854, 4,159,803, 4,300,546, 4,334,531, 4,465,234, 4,632,311, 4,338,576, and 4,850,534. Ultrasonic fluid ejection devices configured for delivery of topical solutions to the surface of the eye have also been developed. See e.g., United States Published Patent Application Publication Nos.: 2014/0336618 and US2013/017283A1; as well as U.S. Pat. Nos. 8,684,980; 8,733,935; and 9,087,145.

While the development of ultrasonic delivery devices such as described above has improved administration of fluids, such as ophthalmic fluids, fluid ejected from these ultrasonic devices is at relatively high velocity, which can result in ocular discomfort during delivery. As such, there is a continued need for improvement.

SUMMARY

Topical ocular delivery devices are provided. Aspects of the devices include a transducer configured to oscillate at an amplitude and frequency which provides for an emitted stream velocity that results in minimal discomfort during topical ocular delivery. In some instances, the transducer is configured to oscillate at higher amplitude and lower frequency as compared to ultrasonic fluid ejection devices, such that the velocity of the fluid stream emitted from the nozzle is substantially lower as compared to that emitted from ultrasonic dispensers. Consequently, the impact of the fluid on the eye is reduced and the discomfort associated with topical delivery is significantly improved.

DETAILED DESCRIPTION

Figure 1:
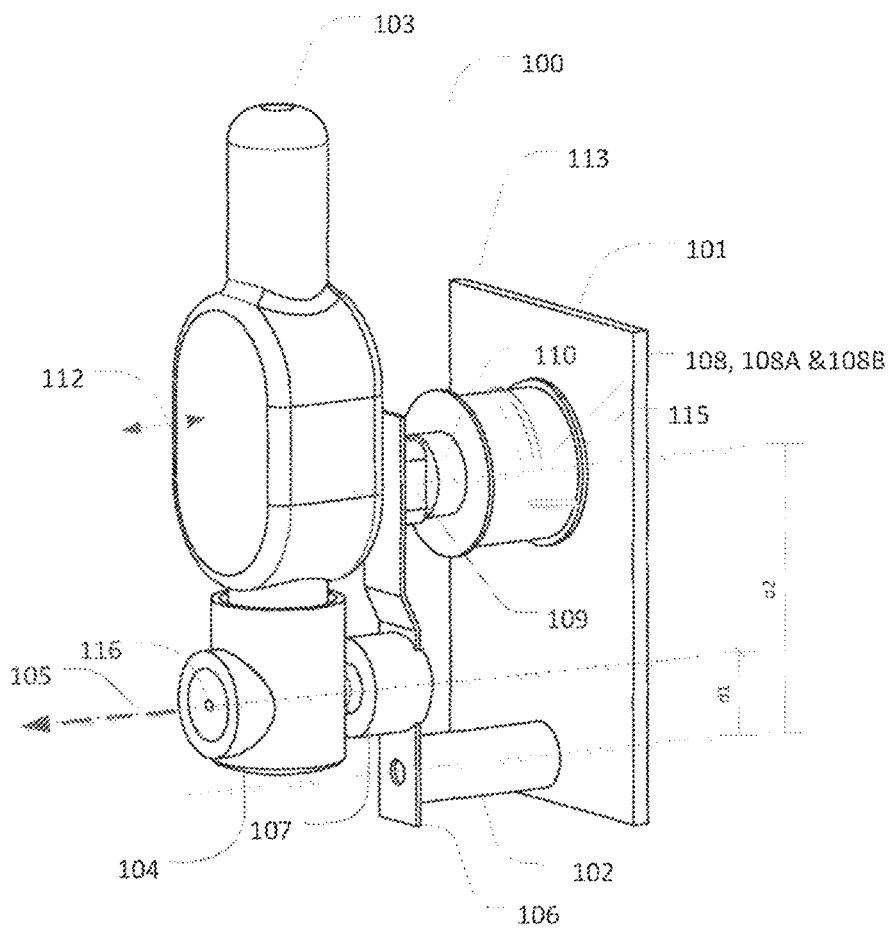
FIG. 1 illustrates a perspective view of an embodiment of the invention.

Fluid ejection devices for delivery of a topical ophthalmic solution to the surface of the eye are provided. Aspects of the invention include a transducer configured to emit a low velocity stream such that the impact force of the fluid against the surface of the eye is reduced or minimized. Also provided are methods of using the devices, e.g., in topical ocular delivery applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various aspects of the invention, embodiments of the devices will be described first, followed by a description of embodiments of methods of using the devices, e.g., in topical ocular delivery applications.

Fluid Delivery Devices

As summarized above, aspects of the invention include fluid delivery devices configured to eject an ophthalmic formulation onto a target location of an eye of a subject, i.e., a target ocular location. The fluid delivery devices are, in some instances, configured to provide for self-administration of a fluid by a user to a target location of the user, e.g., a target ocular location. As such, the devices of such embodiments allow the user to administer a volume of fluid to a target location of the user without any assistance from another individual, such as a health care practitioner.

While the nature of the fluid delivery devices may vary, in some instances the devices are handheld devices. By handheld device is meant that the device is dimensioned and has a weight such that it may be comfortably held by an average adult human hand. In some instances of handheld devices, the device has a longest dimension ranging from 10 to 500 mm, such as 20 to 250 mm, including 50 to 100 mm, such as 70 to 85 mm, and a weight ranging from 10 to 1000 g, such as 25 to 500 g, e.g., 40 to 100 g.

The fluid delivery devices described herein may include a fluid package, which may include a reservoir and an aperture, and a transducer (i.e., actuator) component configured to eject fluid from the reservoir through the aperture. Additional components may also be present. Each of these components is now reviewed in greater detail.

Fluid Package

The fluid package component of devices of the invention is a fluid container that is configured to hold an amount of fluid and be operably coupled to an actuator, e.g., as described in greater detail below. The container may have any convenient configuration, and may be made of any convenient material, e.g., glass or plastic. The container may be configured to hold a single delivered dosage or multiple deliver delivered dosages, e.g., where the container comprises a volume of the liquid formulation sufficient to provide multiple delivered dosages, such that the reservoir is a multi-dose reservoir. As such, the volume of liquid formulation that the container is configured to hold may vary, ranging in some instances from 100 µl to 10 ml, such as 100 to 2000 µl, including 120 to 800 µl.

The container includes a reservoir component configured to hold an amount of a fluid, e.g., as described above, and one or more apertures through which fluid from the reservoir component may be ejected during use. While the number of apertures that a given fluid package has may vary, in some instances the number of apertures ranges from 1 to 20, such as 1 to 10, including 1 to 5, e.g., 1 to 4, 1 to 3, and 1 to 2. In some instances, the fluid package includes a single aperture. In some instances, the fluid package includes more than one aperture. The dimensions of a given aperture may vary, as desired. In some instances, the apertures have a longest dimension, e.g., diameter, ranging from 10 to 500 µm, such as 50 to 450 µm, e.g., 75 to 350 µm, where in some instances the apertures have a diameter ranging from 80 to 120 µm (such as 80 to 100 µm), or 150 to 350 µm (such as 200 to 350 µm, e.g., 250 to 300 µm). Where desired, the aperture may include an antimicrobial material associated with at least a portion thereof, such as a portion or all of the internal surface of the aperture that is configured to mate with the closure when in the sealed configuration. Examples of antimicrobial materials that may be present include, but are not limited to, antimicrobial metals, e.g., silver, copper, etc., antimicrobial coatings, e.g., parylene polymers, chlorhexidine and protamine sulfate compositions, and the like.

While the container may have any convenient configuration, in some instances the container includes an expanded, e.g., bulb, portion that includes the reservoir and a neck portion, e.g., that is configured to operably couple to an actuator and includes the one or more apertures. The fluid package is, in some instances, configured to be disposable. Fluid packages finding use in embodiments of the invention are further described in international application serial no. PCT/US2018/014211 published as WO 2018/136618, the disclosure of which is herein incorporated by reference.

The fluid present in the fluid package may vary, as desired. In some instances, the fluid present in the fluid delivery package is a liquid formulation of an active agent. The terms "agent," "compound," and "drug" are used interchangeably herein to refer to a molecule or molecular combination that has a physiological effect upon contact with a subject via administration to the target topical location of the subject. Examples of active agents that may present in the liquid formulation include, but are not limited to: anti-infectives (including but not limited to antibiotics, antivirals, etc.), anti-inflammatories (including but not limited to steroids and non-steroidal anti-inflammatory drugs (NSAIDS), etc.), anti-allergy agents (including but not limited to anti-histamines and mast cell stabilizers, etc.), anti-fungals, cholinergic agents, anti-cholinergic agents including both long acting and short acting agents (e.g., atropine, tropicamide, etc.), vasoconstrictors, biologics (e.g. proteins, engineered proteins, etc.), small molecules, anesthetics, analgesics, intraocular pressure lowering agents (including but not limited to prostaglandin analogs, ROK inhibitors, beta blockers, carbonic anhydrase inhibitors, and alpha agonists, etc.), lubricants (including but not limited to saline, polymer solutions, proteoglycans, glycosaminoglycans, carbohydrates, etc.), mydriatic (pupil dilating) agents, miotic agents (pupil constricting agents), iodine derivatives, anti-inflammatory/immuno-modulatory/immunosuppressive agent, e.g., a cyclosporine, such as cyclosporine A and derivatives thereof, FK-506, rapamycin, buspirone, spiperone, and/or their derivatives, lifitegrast (Xiidra), etc.; and/or various combinations thereof. Additional drugs and agents which may be utilized with the devices described may include any number of the agents disclosed in further detail in U.S. Pub. 2017/0344714 and U.S. Pat. No. 9,087,145 the disclosures of which are herein incorporated by reference. The concentration of the cholinergic agent in a given liquid formulation of a micro-dose may vary. In some embodiments, the concentration of cholinergic agent in the liquid formulation of the micro-dose ranges from 50 ng/ml to 100 mg/ml.

In addition to the active agent, the liquid formulation may include an aqueous delivery vehicle, e.g., a pharmaceutically acceptable aqueous vehicle. In addition to water the aqueous delivery vehicle may include one or more additional components, including but not limited to: salts, buffers, preservatives, solubility enhancers, viscosity modulators, colorants, etc. Suitable aqueous vehicles include sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, e.g., pH adjusting agents such as sodium hydroxide, hydrochloric acid or sulfuric acid; and viscosity increasing agents such as methylcellulose.

Transducer

In addition to the fluid package, the device further includes an transducer (i.e., actuator) component configured to operably couple to the fluid package and eject fluid from the reservoir of the fluid package through the one or more apertures to the target location. In some instances, the transducer is a component that is configured to impart vibration to the contents of the container, where the oscillation frequency of the vibration may vary. In some instances, the frequency is in the audible range, such as from 20 to 20000 Hz, e.g., 50 to 10000 Hz, such as 50 to 5000 Hz including 100 to 3000 Hz, such as 500 to 3000 Hz, where in some instances the frequency ranges from 800 to 1200 Hz, such as 900 to 1100 Hz, e.g., 1000 Hz. In some instances, the transducer is configured to operate at an oscillation amplitude sufficient to provide the desired fluid velocity, where the oscillation amplitude in some embodiments ranges from 1 to 10 µm, such as 2 to 10 µm, including 1 to 5 µm, such as from 1.5 to 4.5 µm, e.g., 2 to 4 µm and including 2 to 3 µm. In some instances the transducer is characterized by operating at a low intensity of sound, e.g., where the intensity of sound is 50 dB or less, such as 40 dB or less, including 30 dB or less, such as 25 dB or less, including 20 dB or less.

In some instances, the transducer is configured to produce pressure fluctuations in the fluid inside of the fluid package so as to eject fluid from the reservoir through the aperture. In some instances, the transducer produces pressure fluctuations in the fluid by displacement induced on an external surface of the fluid package. The oscillations, e.g., of audible frequency (such as described above), imparted by the transducer on the fluid package, and in some instances the outer surface of the fluid package, produces cycles of acoustic pressure in the fluid held by the fluid package, resulting in ejection of fluid from the one or more apertures.

In some instances, the fluid is ejected from the fluid package by the actuator as a stream, where the stream may be a continuous stream of liquid (i.e., a stream that is not made up of individual droplets) or a discontinuous stream of liquid, e.g., a collimated stream of individual droplets, a series of streams, etc. As the stream, whether continuous or discontinuous, may be collimated, in certain embodiments the liquid formulation contacts a limited portion of the external surface of the eye before spreading across more of the eye surface, where is some instances the limited contact portion is 50% or less, such as 40% or less, including 30% or less, e.g., 25% or less, 20% or less, 15% or less, including 10% or less, e.g., 5% or less of the external surface of the eye. Embodiments of the invention provide for accurate delivery of the stream to a defined location, such that the stream is precisely administered to a desired location of the ocular surface. As the stream may be delivered as a collimated stream, in such instances substantially all, if not all, of the liquid formulation released from the device is delivered to the ocular surface, in contrast to other delivery modalities such as mists and aerosols where not all of the fluid emitted from the device reaches the ocular surface, but instead at least some of which is applied to the surrounding periocular surfaces. Where the stream is a continuous stream of liquid, the stream diameter may vary, and in some instances ranges from 0.05 to 0.50 mm, such as 0.070 to 0.130 mm. In some instances, the stream diameter is substantially constant along its length from its origination point to the topical ocular location, such that any magnitude of difference in diameter is, in some instances, 1 mm or less, such as 0.5 mm or less, e.g., 0.25 mm or less. In such instances, the stream may be collimated, such that it spreads minimally, if at all, as it propagates from the orifice of the device to the ocular surface. Where the stream is a discontinuous stream of individual droplets, the volume of the individual droplets may vary, ranging in some instances from 50 to 1500 µl, such as 100 to 1000 µl. Where droplets are administered, the diameter of a given droplet may vary, ranging in some instances from 20 to 1000 µm, such as 50 to 750 µm, including 100 to 500 µm. The duration of stream delivery during a given administration event may vary and is selected so as to provide the desired delivered micro-dose, e.g., as described above. In some instances, the duration of stream delivery, i.e., the duration of administration, ranges from 20 to 2000 msec, such as 50 to 1000 msec, including 75 to 500 msec, such as 50 to 200 msec, including 100 to 150 msec. The volume that is delivered may be varied as a function of pulse duration, where the pulse duration may be fixed or variable.

As summarized above, the actuator is configured to eject fluid at a velocity that results in minimal, if any, discomfort to the user during administration. The velocity of the administered stream may vary and is generally above the minimum exit velocity of the fluid from the aperture of the device used to administer the stream, e.g., as described in greater detail below. The "minimum exit velocity" is as defined in Linblad and Scheider, "Production of uniform-size liquid droplets," J. Scientific Instruments (1965) 42: 635. (see equation 2 described therein). In some instances, the exit velocity is 20% or more above the minimum exit velocity and in some instances is 300% or less above the minimum exit velocity. For example, for an aperture size of 150 micron the minimum exit velocity is 194 cm/sec but the selected velocity may be at least 30% higher, i.e. at least 252 cm/sec. In some instances, the velocity ranges from 10 to 500 cm/sec, such as 20 to 250 cm/sec and including 50 to 150 cm/sec.

While the nature of the transducer component may vary, in some instances the transducer component is an electromagnetic actuator. In some embodiments, an electromagnetic transducer imparts an oscillation amplitude at low frequency, which in some instances is within the audible range (e.g., 20 to 20,000 Hz). In some instances, the electromagnetic transducer operates in the audio range of frequencies, but produces low audible tone, generally 30 dB or lower. At the same time, the device emits fluid from a sufficiently large nozzle at sufficiently low velocity to minimize the discomfort associated with topical delivery to the eye. While the electromagnetic transducer may vary, in some instances the electromagnetic transducer includes a configuration that amplifies the oscillation force applied to the drug package. In some instances, the electromagnetic transducer includes a cantilever beam that is constrained at one and has a permanent magnet positioned at the other end, where the drug package is attached in the proximity of the constrained end, e.g., as illustrated in the figures and described in greater detail below.

Illustrative Embodiment

As discussed above, the minimum fluid velocity required for formation of a stream emitted from an aperture is inversely proportional to its diameter (N R Lindblad and J M Schneider 1965 *J. Sci. Instrum.* 42 635 *Production of uniform-sized liquid droplets*). In embodiments of the present invention, the nozzle diameter of about 0.2 mm is at least two times larger than that described in prior art ophthalmic delivery systems, as disclosed in U.S. Pat. Nos. 5,630,793; 9,087,145 and 8,684,980. A larger diameter nozzle was selected to reduce the fluid velocity impacting the surface of the eye. A larger diameter stream at lower velocity exerts lower pressure (force per unit area) on a target surface, which may be more comfortable to patients.

The minimum oscillation amplitude required to dispense fluid from such a large nozzle is relatively high, approximately 3 μm. Such amplitude is hard to generate at ultrasonic frequency, e.g., above 20,000 Hz. However, it can be readily achieved at lower frequencies, e.g., below 3,000 Hz or even at 1,000 Hz. The present invention describes a transducer, such as an electromagnetic transducer (i.e., actuator), that operates in the audio range of frequencies, but produces low audible tone, which is in some instances is 30 dB or lower. At the same time, the device emits fluid from a sufficiently large nozzle at sufficiently low velocity to minimize the discomfort associated with topical delivery to the eye. In addition, due to the large diameter of the aperture, the device can deliver required volume in a shorter period on time. In some instances, devices of the invention can deliver about 5-10 μl within 500 msec, such as within 250 msec. Additionally, due to the larger diameter of the aperture, the device can dispense viscous fluid, e.g., in the range of 1-20 centipoise.

In embodiments of the present invention the diameter of the aperture is in some instances 200 μm or greater. Referring back to the article cited above, the minimum exit velocity that is required to form a jet is inversely proportional to the nozzle diameter. The minimum velocity is defined in the equation below $$V > 2\sqrt{\frac{T}{0866 * D * \rho}}. \qquad 1$$

Wherein V is the minimum exit velocity,
T is the surface tension of water at 25° C. T=72 dyne/cm
D is the nozzle diameter
$\rho$ is the density of the water $\rho=1$ gm/cm$^3$ Thus, for example, when the nozzle diameter is 100 μm, as defined in prior art, such as U.S. Pat. Nos. 5,630,793, 9,087,145 and 8,684,980, the lowest possible velocity based on equation 1 is about 1.82 m/sec. However, when the nozzle diameter is 200 μm the velocity is 1.29 m/sec, thus the impact pressure of the fluid against the surface of the eye is proportionally reduced due to (1) reduced velocity and (2) 4 times larger area of the jet.

Figure 2:
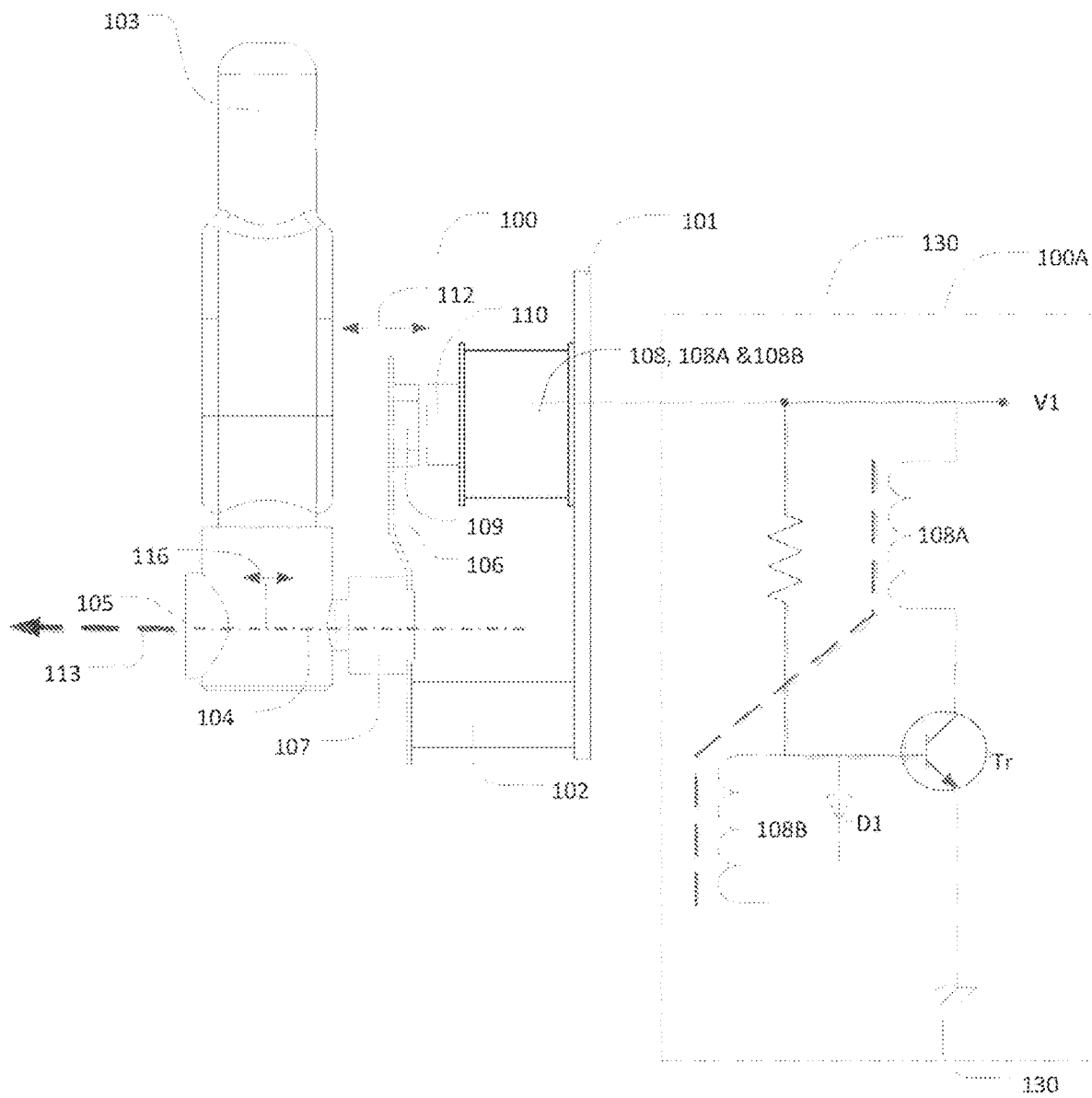
FIG. 2 illustrates a side view of the embodiment of FIG. 1, as well as the electronic circuit thereof.
Figure 3:
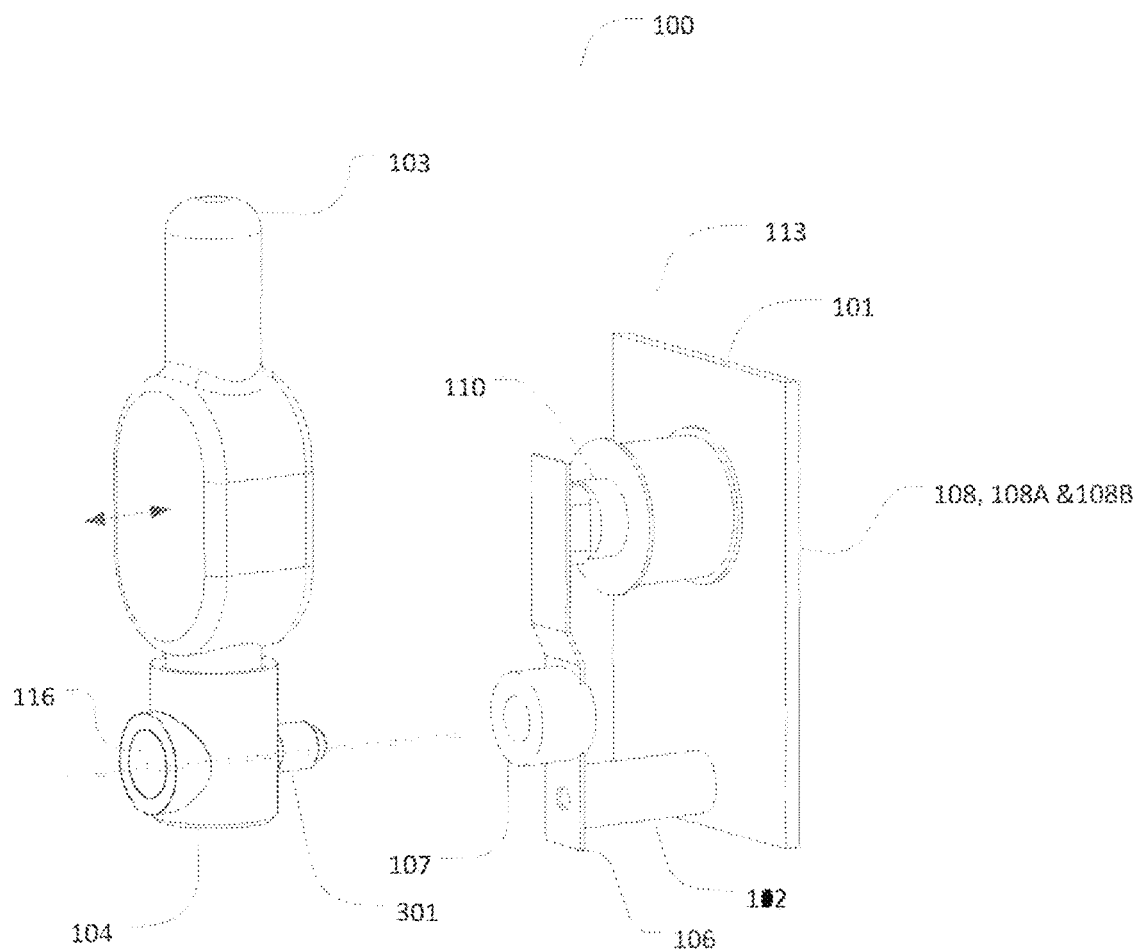
FIG. 3 illustrates an exploded view of the embodiment of FIG. 1 and FIG. 2 showing the ampule and the magnetic transducer separately.

An embodiment of the invention is illustrated in FIGS. 1 to 3. Referring to FIG. 1, which illustrates the electromagnetic dispensing device (100) of the present invention. Device (100) includes an ampoule (103) containing a fluid to be dispensed and further includes an electromagnetic transducer (113) that is configured to oscillate the ampoule such that the fluid is dispensed through aperture (116) at the lower part of the ampoule.

Transducer (113) comprising a base plate (101), electromagnet (115) and a permanent magnet (109). Electromagnet (115) comprising a ferromagnetic core pin (110) and a coil (108) that is wound around the core pin. Permanent magnet (109) is positioned in a close proximity to the electromagnet core pin (110) and is suspended by a flexible cantilever beam (106) having a free end and a constrained end. The dimensions of cantilever beam (106) may vary, where in some instances the cantilever beam has a width ranging from 2 to 8 mm, such as 3 to 7 mm, including 4 to 6 mm (e.g., 5 mm) and a length ranging from 15 to 25 mm, such as 15 to 20 mm, including 16 to 18 mm (e.g., 17 mm), where in some instances the dimensions of the beam are chosen in conjunction with oscillating amplitude to provide a device that operates desirably soft sound, e.g., as described above, such as less 30 dB or less. Alternating magnetic field generated by coil (108) produces magnetic force and mechanical oscillations of permanent magnet (109) and the flexible cantilever beam (106) that supports it. Cantilever beam includes an anchor (107) which support and transmits the oscillation of the cantilever beam to the ampoule. Cantilever beam (106)

having a constrained end and a free end enables the electromagnetic transducer to produce sufficient force to oscillate the drug package. In the illustrated embodiment, the magnet is attached to the free end but the drug package is attached close to the constrained end, e.g., within 5 mm or less, such as 2 mm or less, including 1 mm or less. As such, the oscillation force that is applied to the drug package is amplified by the mechanical advantage afforded by the cantilever configuration which allows the electromagnetic transducer to impart sufficient force on the drug package. Furthermore, the high amplitude oscillation of the magnet at the free end is fed back to the circuit (by the magnetic field). In some instances, this configuration results in the circuit operating at its natural frequency. This configuration provides for a device which is extremely economical and yet provides an effective approach to delivering drug to the surface of the eye. The device further includes a standoff support pin (102) that extends from the base plate (101) and provides a support to the cantilever beam (106). In yet other configurations, the oscillator many not operate at its natural frequency.

In the illustrated embodiment, permanent magnet (109) is positioned at the free end of cantilever beam at a distance of (d2) from the cantilever beam support (102) while the ampoule support anchor (107) is at a distance of (d1) from the beam support (102). In this way a mechanical advantage is obtained, and the force applied to the ampule is amplified by the ratio of the distances d2/d1 relative to the force applied to the permanent magnet. In the illustrated embodiment the ampoule contains 1 mL of aqueous solution and has a mass of approx. 1 gm. Accordingly, the force that is required to oscillate the ampoule at an amplitude of approximately 20-60 mm is about 0.2N to 1N. In the illustrated embodiment, the distance d2 is 13.5 mm and distance d1 is 1.35 mm. The ratio d2/d1 is about 10, and the oscillation amplitude is between 20 µm to 60 µm, depending on the input voltage. In the illustrated embodiment, the diameter of the dispensing aperture ranges between 200 and 350 µm, and such large aperture dispenses only at high oscillation amplitude.

In the illustrated embodiment the ferromagnetic core (110), base plate (101) and support pin (102) are made of a soft magnetic material, such as 4750 alloy, or other alloys that have low corrective force and minimal magnetic hysteresis can be used.

Ampoule (103) is oriented such that the dispensing nozzle (116) is aligned with the oscillation amplitude of the cantilever beam (106). The oscillations generate pressure fluctuation inside the ampoule and fluid is ejected from nozzle (116) as illustrated by the arrow (105)

Permanent magnet (109) may be made of a rare-earth magnetic material, such as Neodymium N35, N38, N42, Samarium Cobalt or the like. Non-rare-earth alloy such as iron, nickel and cobalt may also be used.

Referring now to FIG. 2, this figure shows magnetic transducer (100) and further includes a diagram of the electrical circuit that generates alternating electrical signal from a DC source, such as a battery cell. Electromagnetic transducer (100) includes a circuit (100A) which produces alternating current which is fed to the coil (108) to generate a magnetic force which oscillates permanent magnet (109). Coil (108) defines two separates magnetic coils, the first is primary coil (which may be referred to as the driver coil) (108A) and the second is detection coil (which may also be referred to as sensor coil) (108B). Both coils (108A) and (108B) are wound around the iron core (110). When DC voltage is connected to the primary coil (108A) current flows and the electromagnetic force that is developed pulls permanent magnet (109) toward iron core (110). At the same time the current in the primary coil (108A) produces transient, time-dependent electromagnetic induction, which induces electromotive force (EMF) and electrical current in the detection coil (108B), the current is fed to a bipolar transistor (Tr) which switches off the current from the primary coil (108A) by pulling it to the ground (130). As a result, magnetic force returns to zero and magnet (109) return to its normal position. Subsequently, primary coil (108A) turns on again and pulls back the magnet. In this way the alternating magnetic field is generated using a DC input voltage from a DC battery. Transistor (Tr) is an NPN general purpose amplifier, such as Fairchild model 2N3904. The circuit further includes a Zener diode (D1) that regulates the voltage. Magnetic coils (108A) and (108B) have an inductance that ranges from 1-10 mH and are configured to generate a magnetic field to oscillate the magnet (109). Generally, the mass of magnet (109) is small to reduce the inertial load and increase the oscillation amplitude. In one embodiment, the mass of permanent magnet (109) is 0.075 gm. Beam (106) is made of stainless-steel alloy 304 having a thickness of 0.2 mm, a width of 5 mm and a free length of 13.5 mm. In the illustrated embodiment, the beam has a natural frequency of about 523 Hz while the driving frequency of magnetic oscillator is about 1100 Hz.

While FIG. 2 illustrates an oscillator based on coaxial primary (i.e., driver) and detection (i.e., sensor) coils, alternative configurations may also be employed. For example, in some instances only a primary or drive coil is present, and a detection or sensor coil is not present. In such instances, the direction of the current in the primary coil may be reversed to obtain the desired oscillation frequency. In other words the current may be switched from positive to negative at a desired frequency to obtain the desired oscillation. The direction of the current in the primary or drive coil may be switched using any convenient approach, e.g., with a frequency generator, oscillatory, microprocessor etc., which may be operatively coupled to the primary or drive coil, e.g., with a square bridge circuit, etc.

FIG. 3 illustrates an exploded prospective view of the dispensing device (100), showing the ampoule (103) and the electromagnetic transducer (113) separately. It can be seen that ampule (103) includes a pin member (301) that is inserted into anchor member (107) in a tight interference fit. In this way the oscillations that are generated by the transducer are transmitted to the ampoule Where desired, the fluid delivery devices may include one or more additional components, e.g., as described below.

Alignment System

Embodiments of the fluid delivery devices described herein may also include an image-based alignment system configured to align fluid ejected through the one or more apertures of the fluid package with a target location, such as a target ocular location (e.g., as described in greater detail below). The alignment systems are systems that allow user, such as the subject to which the fluid is to be administered, to align the one or more apertures with the target location such that the ejected fluid is delivered to the target location upon actuation of the device. The alignment system is, in some instances, configured so that a user may self-administer the fluid from the device following alignment by the user of the device, e.g., by a protocol described in greater detail below.

As summarized above, the alignment systems are image-based alignment systems. By "image-based" alignment system is meant that alignment of a delivery device with a target location includes visualization of an image, e.g., a picture or a reflection, by a user, e.g., the subject to which fluid is delivered during a self-administration protocol.

Lenticular Print Image-Based Alignment System

In some instances, the image-based alignment system is a system that includes one or more lenticular prints. A lenticular print may include one or more printed images and an array of linear lenses or focusing elements which are overlaying the images. Due to the optical characteristic of the lenses or focusing elements, a portion of the printed image is forms desirable synthetic visible image only from a certain angle. In one embodiment, the fluid delivery device and the lenticular print are positioned such that when the image is visible to the user the stream from the delivery device will reach the target location, such as the surface of the eye. The alignment system may include lenticular prints wherein one pair of linear lenses is perpendicularly positioned relative to a second pair of linear lenses. In this way rotational or angular alignment is achieved with respect to the two axes that are perpendicular to the line of sight or the optical axis of the eye.

In one embodiment, the alignment system includes two pairs of lenticular prints. One pair of prints has an array of vertical linear lenses and a second pair of prints has an array of horizontal linear lenses. The prints of the vertical pair are placed a predetermined distance from each other and the prints in the horizontal pair are positioned a predetermined distance from each other. In this way the desired image is visible to the user only from a certain distance and only in one orientation. The dispensing device and the lenticular prints may be in a position in placement relationship to each such that when the desired image is visible to the user the stream that emits from the dispensing device reaches the target location, e.g., target ocular location. In some instances, the desired image is visible when the delivery device is placed about 50 to 100 mm from the target location. In one alternative embodiment the lens or focusing element comprising an array of lenses or a focusing element and an image-forming system that includes or is formed from an array or pattern designed to collectively form an image or a certain desired pattern only from a predetermined distance and orientation relative to the one or more orifices.

Any convenient lenticular system such as described above may be employed, where examples of such lenticular systems include, but are not limited to, those described in U.S. Pat. Nos. 6,065,623 8,144,399, as well as international patent publication no. WO1994020875; the disclosures of which are herein incorporated by reference. Systems of lens arrays are described in published United States Patent Publication Nos. 2015/0276994, 2015/0256730, 2015/0036219 and 2015/0035180, the disclosures of which are herein incorporated by reference.

Reflective Surface Image-Based Alignment System

Another type of image-based alignment system that may be present in fluid delivery devices of the invention is a reflective surface (i.e., mirror) image-based alignment system, where such systems include one or more reflective surfaces or mirrors, and in some instances include a single reflective surface or mirror. In some instances, the reflective surface has a curved shape which defines a focal point, i.e. comprising a concave mirror.

Typically, the most visible parts of the eye, when looking in a mirror, are the iris, conjunctiva, sclera (through the conjunctiva), and cornea. Ocular tissue in the focal plane of the concave spherical mirror will appear in focus when the mirror is placed at the focal distance (F) from that tissue. The focal point (P) is the intersection of the focal plane with the optical axis of the mirror. One method for delivering fluid to a targeted region may generally comprise positioning a reflective surface having a curved shape into proximity with the targeted region located upon a surface of an eye until a reflection of the eye in the reflective surface appears focused to a subject, wherein a focal plane defined by the reflective surface is coincident with the eye when the reflection appears focused. Once positioned, the method may include actuating a fluid delivery assembly to emit a fluid from one or more apertures so that fluid is delivered to the target location on the eye.

In some instances, the reflective surface defines one or more openings therethrough. In such systems, the system may also include a fluid delivery assembly configured to emit a fluid from one or more apertures which are aligned with the one or more openings, wherein the system is configured to emit the fluid through the one or more openings and towards or in proximity to the focal point. In some instances, the fluid delivery assembly is configured to emit a fluid from one or more apertures which are aligned with one or more openings defined through the reflective surface such that the fluid is directed towards or in proximity to the focal plane and upon the targeted region. In another variation, a system for aligning a fluid delivery assembly relative to a targeted region on an eye of a subject may generally comprise a concave mirror having a reflective surface, wherein the mirror defines a focal plane and one or more openings through the mirror for fluid delivery, and a fluid delivery assembly configured to emit a fluid from one or more apertures which are aligned with the one or more openings such that the fluid is ejected through the one or more openings and towards or in proximity to the focal plane.

Instead of a concave mirror, the reflective imaging assembly may include a flat mirror coupled with a suitable lens that provides for alignment by a user, e.g., as described above and in greater detail below.

Whether the reflective surface is curved or flat, the alignment system may be configured such that in self-administration protocols where the target location is an ocular surface, the user may focus an image of the eye that includes the target location when aligning the fluid delivery device. As such, the same eye that includes the target ocular location is employed by the user to align the fluid delivery device, e.g., by focusing and centering the eye in the mirror of the alignment system.

The dimensions of the reflective surface of such image-based alignment systems may vary, as desired. In some instances, reflective surface has a longest dimension, e.g., diameter, that ranges from 10 to 30 mm. In some instances, the dimensions are such that a subject does not view the entire eye that includes the target ocular location in the mirror. In such instances, the longest dimension, e.g., diameter, may range from 10 to 15 mm, such as 10 mm, 11 mm, 12 mm, 13 mm, 14 mm or 15 mm.

Housing

In some embodiments, the fluid delivery devices include a housing with which the various components of the device, e.g., as described above, are associated. The housing may have any convenient configuration, and in some instances has a longest dimension ranging from 50 to 100 mm, such as 70 to 85 mm. The housing may have any convenient shape, where shapes of interest include those that allow for ready handling and use of the device. In some instances, the housing has an approximately rectangular cuboid shape. The housing may be fabricated from any convenient material, such as a plastic or metal material.

While the various components of the device may be associated with the housing component in any convenient manner, in some instances the fluid package and actuator components are present inside the housing, and least a portion of the image-based alignment system is associated with a surface of the housing, e.g., so that the image-based alignment system may be viewed by a user during use.

In some instances, the housing includes a movable cover, e.g., which covers the apertures and/or alignment system when the device is not in use. The cover may be configured to move between closed and open positions, where upon moving the cover from the closed to the open position, the device is transitioned to a configuration where it may be employed to deliver fluid. In some instances, movement of the cover from the closed to the open position may result in the device transitioning from an inactive to active state. For example, movement of the cover from the closed to the open position may results in activation of the actuator component.

Illumination Source

In some instances, the device includes one or more illumination sources. Any convenient illumination source may be employed, where such sources include, but are not limited to, light emitting diodes (LEDs), and the like. When present, the illumination source may take a variety of different configurations. For example, it may be distinct from any other component of the device, such as the alignment system. Alternatively, it may be associated with another component of the device. For example, it may be associated with the alignment system of the device, such as at least partially bounding, if not completely bounding the alignment system of the device. When present, the illumination source may serve a variety of different functions, such as illuminating the target location in a reflective surface of the alignment system, indicating that the device is aligned with the target location, indicating that the device is within a predetermined distance of the target location, indicated that the device is ready to deliver fluid, indicating the amount of fluid in the fluid package (e.g., full, partially full, empty), and the like.

Distance Sensor

In some instances, the device includes one or more distance sensors. A distance sensor is a component configured to determine the distance between the device and the target location. Any convenient distance sensor may be present, where such sensors include, but are not limited to, infra-red (IR) sensors, radar sensors, and the like. In some instances where the device includes a distance sensor, the device may further be configured to provide a signal, such as an auditory or visual signal, when the determined distance between the device and the target location is within a predetermined range. For example, the device may be configured to activate an illumination source, e.g., as described above, when the device is within a predetermined range of the target location as determined by the distance sensor. In some instances, the device is configured to be activated when the determined distance between the device and the target location is within a predetermined range. In the above embodiments, the predetermined range may vary, and in some instances is between 1 mm and 250 mm, such as 10 mm to 100 mm.

Figure 4:
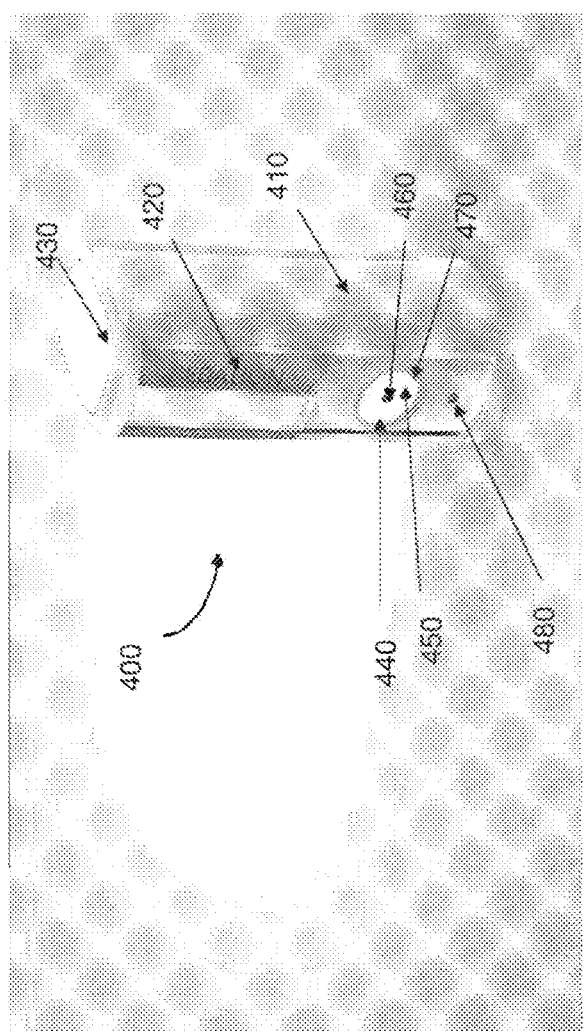
FIG. 4 provides a view of a fluid delivery device in accordance with the invention.

FIG. 4 provides a view of a fluid delivery device in accordance with the invention. As shown in FIG. 4, device (400) includes a housing (410) having a sliding cover (420). Present in the housing a fluid delivery package and transducer, e.g., as described above. As shown, the device (400) includes an actuator button (430) on the top of the housing. The device also includes a concave-mirror image-based alignment system (440) as described above, where the concave mirror (450) includes an opening (460) through which fluid ejected from the aperture may flow during fluid delivery. Surrounding or bounding the concave mirror (450) is circular LED (470). Also shown is IR sensor (480).

Further details regarding various embodiments of the above components are provided in U.S. patent application Ser. No. 14/992,975 filed Jan. 11, 2016 and published as U.S. Pat. Pub. 2016/0199225; U.S. patent application Ser. No. 15/094,849 filed Apr. 8, 2016 and published as U.S. Pub. 2016/0296367; U.S. patent application Ser. No. 15/874,377 filed Jan. 18, 2018 and published as U.S. Pub. 2018/0207030; International Application Serial No. PCT/US2018/064529 filed Dec. 7, 2018; U.S. Prov. Pat. App. 62/656,552 filed Apr. 12, 2018; and U.S. Prov. Pat. App. 62/693,818 filed Jul. 3, 2018; which applications are incorporated herein by reference.

Methods

As summarized above, aspects of the present disclosure include methods of administering a liquid formulation of an ophthalmic agent to a topical ocular location of an eye of a subject. By topical ocular location is meant a region (i.e., area or domain) of an external surface of an eye, such as a region of a cornea, a region of a conjunctiva, a region that includes both corneal and conjunctival components, etc. In some instances, the topical ocular location is an area or region that is offset relative to the optical axis of the eye. In some instances, the topical ocular location is on either the bulbar or tarsal conjunctiva, or in the conjunctival fornix. In other words, the topical ocular location is one that is displaced from the center of the pupil or the center of the iris. While the magnitude of the distance of the offset/displacement may vary, in some instances the magnitude ranges from 1 to 30 mm, such as 2 to 20 mm, e.g., 5 to 15 mm, including 5 to 10 mm. While the target topical ocular location may vary in size, in some instances the size of the target topical ocular region ranges from 2.5 to 12, such as 3 to 9 mm$^2$.

Aspects of the invention include delivering a dose or volume of the liquid formulation of the ophthalmic agent that can be wholly accommodated by the tear film of the topical ocular location. The tear film of the ocular location is the film that is associated with the topical ocular location. As such, the tear film is the film or layer of tear liquid that is present on the eye surface on which the topical ocular location, e.g., as described above, is located. As the delivered volume of the liquid formulation is a volume that can be wholly accommodated by the tear film of the topical ocular location, it may also be a volume that may be wholly accommodated by the ocular surface that includes the topical ocular location. By "wholly accommodated by the ocular surface" is meant that, upon delivery, the delivered volume is a volume that can be held on the surface of the eye to which it is administered without any excess liquid running off of the surface of the eye and over the eyelid, e.g., in the form of tears. While the volume of a given delivered volume may vary, in some instances the volume ranges from 1 to 15 µl, such as 3 to 10 µl, including 5 to 10 µl. In some instances, the volume of liquid formulation that is administered to the ocular surface does not result in a blinking reflex. As such, delivery of a volume of liquid in accordance with embodiments of the invention does not result in reflex tearing, blepharospasm/blinking, which in embodiments allows for a precise, known amount of active agent to be delivered to the topical location.

An advantage of embodiments of the invention is that because the volume of liquid formulation that is precisely administered to the ocular surface can be wholly accommodated on the ocular surface, exact, known amounts of an ophthalmic agent are delivered to the topical ocular location. As reviewed above, volumes of a liquid formulation are delivered in a manner that minimizes, if not eliminates, reflex tearing and volumetric losses of the liquid formulation. As such, in a given liquid formulation administration, the administered fluid aliquot is exactly what is retained on the ocular surface. Accordingly, methods of the invention allow for delivery of exact known mass amounts of a given ophthalmic agent. In other words, a precise amount of ophthalmic agent is delivered to the ocular surface, in contrast to other administration protocols where a precise, known amount cannot be delivered, predicted or measured because of one or more of loss through reflex blinking or tearing, loss through failure of entire dose to reach ocular surface (e.g., as occurs in delivery of mists or aerosols), etc. In methods of the invention, the amount (mass) of the ophthalmic agent delivered to the ocular surface is a mass equal to the administered volume times the concentration of ophthalmic agent in the administered liquid formulation. For example, if a given administered volume is 10 microliters of a 1% ophthalmic agent (10 mg/mL) solution, then the known mass of ophthalmic agent delivered to the ocular surface is 0.1 mg. Similarly, when delivering 4 microliters of a 2% ophthalmic agent (20 mg/mL) solution in accordance with the invention, the known mass of ophthalmic agent delivered to the ocular surface is 0.08 mg. This ability to know the mass of ophthalmic agent delivered to a topical ocular surface represents a distinct advantage as compared to other methods of delivering active agents to topical ocular locations, e.g., using conventional eye drop protocols or aerosol/mist delivery devices. For example, with a conventional eye drop with a volume of 40 microliters, it is unknown exactly how much of the active agent or drug is actually delivered and maintained on the ocular surface, because (1) the ocular surface cannot hold 40 microliters on its surface, (2) a large portion of the eye drop spills over the lid margin and is wiped with a tissue, and (3) additional drop volume is lost through the lacrimal system, and (4) reflex tearing ensues as a result of the large drop volume and leads to dilution of the drug concentration. With respect to devices that deliver a formulation in mist/aerosol format, not all of the dispensed formulation can be ensured to have landed on the cornea or ocular surface, and not the surrounding periocular surfaces.

While the mass of given ophthalmic agent delivered to a topical ocular location in accordance with embodiments of the invention may vary depending on a number of considerations, including the nature of the agent, the condition to be treated, the age of the subject, etc., in some instances the delivered mass ranges from 0.00001 mg to 10 mg, such as 0.00005 mg to 5 mg, including 0.01 to 1 mg, such as 0.05 to 0.5 mg, including 0.75 to 0.15 mg.

Aspects of the invention include delivering a micro-dose of an ophthalmic agent to a topical ocular location. In some instances, the delivered micro-dose is one that has an efficacy comparable to a reference dosage having a volume that exceeds the capacity of the tear film of the target topical ocular location. The reference dosage in such instances, apart from volume, is otherwise identical to that of the delivered dosage. As such, the concentration of the active agent in the reference dosage is the same as the concentration of the active agent in the delivered dosage. The volume of the reference dosage exceeds that of the delivered dosage, e.g., by 2-fold or greater, such as 3-fold or greater. In some instances, the reference dosage has a volume ranging from 25 to 60 µl, such as 30 to 50 µl. In some instances, the reference dosage is a dosage that is delivered by a standard eye dropper device.

Micro-doses of embodiments of the invention are effective, e.g., to treat an ocular condition for which they are administered, with at least reduced adverse effects, and in some instances without substantial adverse effects, e.g., adverse effects that might otherwise require an additional medicinal agent to counteract the adverse effects and/or result in reduced patient compliance. As such, the magnitude of any adverse effects caused by administration of the micro-doses is reduced and in some instances sufficiently minimal such that no intervention is necessary to ameliorate the adverse effects, e.g., administration of an additional active agent that ameliorates the adverse effects. In some instances, the subject experiences no adverse effects following administration of a micro-dose. As the micro-doses of embodiments of the invention are effective to treat an ocular condition for which they are administered without substantial adverse effects, in some instances the ophthalmic agent is the only active agent present in the micro-dose, such that the micro-dose includes no other active agents, including agents that ameliorate any adverse effects of the ophthalmic agent that treats condition for which it is being administered. For example, where pilocarpine is administered in a micro-dose in accordance with embodiments of the invention, the micro-dose may not include any agents that ameliorate adverse effects of pilocarpine, where such agents include vasoconstrictors, such as oxymetazoline, naphazoline, tetrahydrozoline, and alpha agonists (e.g. brimonidine) and the like.

The ability to deliver precise known amounts in accordance with the invention allows for the delivery of the same dosage or amount of an active agent using a variety of different regimens (the term "regimen" is used its conventional sense to refer to the schedule of doses of an active agent, including the time between doses, the duration of treatment and the amount to be administered each time), where for a given subject a single regimen may be repeatedly used or a number of different regimens may be employed over a given course of treatment. As such, the methods and devices described herein provide for the same dosage of active agent to be delivered by multiple different regimens. For example, with respect to first micro-dose in which a given volume of a drug formulation having a given active agent concentration is administered, the volume of drug formulation and concentration of active agent in the formulation may be varied to obtain a micro-dose that administers the same dosage but by a different regimen. For example, as compared to a first micro-dose, the volume of an active agent formulation that is delivered may be increased and the concentration of active agent in the delivered fluid decreased to the extent that the tolerability and efficacy of the second regimen is superior to that of the first regimen even though the precise dose of active agent administered as determined by weight in micrograms, milligrams or grams of the API is identical amongst the first and second regimens.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

In some aspects of the subject methods, the method further comprises the step of measuring efficacy of a given condition, e.g., of a disease condition in the subject. In some such instances, the determination is made by comparing the results to the results performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more. The evaluation may vary depending on the nature of the condition being treated. In some embodiments, the subject methods further include diagnosing an individual as having a given condition.

Utility

The subject methods devices find use in a variety of different applications, including both treatment and diagnostic/examination applications. The term "treating" or "treatment" as used herein means the treating or treatment of a disease or medical condition in a subject or patient, such as a mammal (such as a human), where the term includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

An example of a condition that may be treated using methods/devices of the invention is glaucoma. Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. In glaucoma associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

In embodiments where the methods and devices are used in treating glaucoma, the delivered dosage may include an intraocular pressure modulatory agent. An "intraocular pressure modulatory agent" can comprise a drug and may be any of the following or their equivalents, derivatives or analogs, including anti-glaucoma medications (e.g. adrenergic agonists, adrenergic antagonists (beta blockers), carbonic anhydrase inhibitors (CAIs, systemic and topical), therapeutic agent(s) such as prostaglandins, prostaglandin precursors, including antiglaucoma drugs including beta-blockers such as timolol, betaxolol, levobunolol, atenolol (e.g., as described in U.S. Pat. No. 4,952,581); adrenergic agonists including clonidine derivatives, such as apraclonidine or brimonidine (e.g., as described in U.S. Pat. No. 5,811,443); and prostaglandin analogues such as bimatoprost, travoprost, tafluprost, latanoprost, etc. In some instances, the therapeutic agent is already marketed for glaucoma, and commercially available preparations thereof can be used. Further therapeutic agents include carbonic anhydrase inhibitors such as acetazolamide, dorzolamide, brinzolamide, methazolamide, dichlorphenamide, diamox; and the like.

Other disease conditions that may be treated by methods and devices of the invention include, but are not limited to, those described in U.S. Pub. 2017/0344714 and U.S. Pat. No. 9,087,145 the disclosures of which are herein incorporated by reference.

Diagnostic/examination applications include, but are not limited to, mydriasis applications where the pupil is dilated, e.g., to permit examination of the retina and other deep structures of the eye. Mydriatic agents that may be employed in such applications include, but are not limited to: atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, and tropicamide hydrochloride.

Kits

Also provided are kits that find use in practicing embodiments of the methods, such as those described as described above. The term "kit" refers to a packaged delivery device or component thereof, e.g., ampule, such as described above. In addition to the above-mentioned components, kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Notwithstanding the appended claims, the disclosure is also defined by the following clauses:

1. A fluid delivery device, the device comprising:
   (a) a fluid package comprising:
      (i) a reservoir comprising an ophthalmic formulation; and
      (ii) an aperture; and
   (b) an electromagnetic transducer configured to oscillate at a frequency sufficient to eject fluid from the reservoir through the aperture at a velocity which results in minimal discomfort during topical ocular delivery.
2. The fluid delivery device according to Clause 1, wherein the electromagnetic transducer is configured to produce pressure fluctuations in the fluid so as to eject fluid from the reservoir through the aperture.
3. The fluid delivery device according to Clause 2, wherein the electromagnetic transducer produces pressure fluctuations in the fluid by displacement induced on an external surface of the fluid package.
4. The fluid delivery device according to any of preceding clauses, wherein the electromagnetic transducer oscillates at an audible frequency.
5. The fluid delivery device according to Clause 4, wherein the audible frequency ranges from 50 to 5,000 Hz.
6. The fluid deliver device according to Clause 5, wherein the audible frequency ranges from 800 to 1200 Hz.
7. The fluid delivery device according to any of the preceding clauses, wherein the electromagnetic transducer is configured to operate at an oscillation amplitude ranging from 2 to 3 μm.
8. The fluid delivery device according to Clause 7, wherein the electromagnetic transducer comprises an electromagnet and a permanent magnet in operational proximity to each other.
9. The fluid delivery device according to Clause 8, wherein the permanent magnet is positioned at a first region of a cantilever beam.
10. The fluid delivery device according to Clause 9, wherein the electromagnetic transducer further comprises an anchor positioned at a second region of the cantilever beam and configured transmit oscillatory displacement force to an external surface of the drug package.
11. The fluid delivery device according to any of the preceding clauses, wherein the electromagnetic transducer is reusable.
12. The fluid delivery device according to any of the preceding clauses, wherein the fluid package comprises an expanded region comprising the reservoir and a neck region comprising the aperture.
13. The fluid delivery device according to any of the preceding clauses, wherein the aperture has a diameter ranging from 200 to 350 μm.
14. The fluid delivery device according to any of the preceding clauses, wherein the reservoir is a multi-dose reservoir.
15. The fluid delivery device according to any of the preceding clauses, wherein the fluid package is disposable.
16. The fluid delivery device according to any of the preceding clauses, wherein the device is configured to eject fluid through the aperture as a stream having a velocity ranging from 50 to 150 cm/s.
17. The fluid delivery device according to any of the preceding clauses, further comprising an image-based alignment system configured to align fluid ejected through the aperture with a target ocular location.
18. The fluid delivery device according to Clause 17, wherein the image-based alignment system comprises a reflective surface.
19. The fluid delivery device according to any of the preceding clauses, wherein the fluid package and electromagnetic transducer are present in a housing.
20. The fluid delivery device according to Clause 19, where the housing comprises a cover positioned along the housing, wherein the cover is configurable between an open position, in which the one or more apertures are exposed, and a closed position, in which the one or more apertures are not exposed.
21. The fluid delivery device according to Clause 20, wherein the cover comprises a sliding cover structure.
22. The fluid delivery device according to Clause 21, wherein the electromagnetic transducer is configured to be activated when the cover is in the open position.
23. The fluid delivery device according to Clause 22, wherein the electromagnetic transducer is configured to be deactivated when the cover is in the closed position.
24. The fluid delivery device according to any of the preceding clauses, wherein the device comprises an illumination source.
25. The fluid delivery device according to any of the preceding clauses, wherein the device further comprises a distance sensor configured to determine the distance between the device and a target location.
26. A method of delivering a fluid to a target site of a subject, the method comprising:
   (A) aligning a fluid delivery device with the target site, wherein the fluid delivery device comprises:
      (1) a fluid package comprising:
         (a) a reservoir comprising an ophthalmic formulation; and
         (b) an aperture; and
      (2) an electromagnetic transducer configured to oscillate at a frequency sufficient to eject fluid from the reservoir through the aperture at a velocity which results in minimal discomfort during topical ocular delivery; and
   (B) activating the electromagnetic transducer to eject fluid from the reservoir through the aperture to the target location at a velocity which results in minimal discomfort during topical ocular delivery.
27. The method according to Clause 26, wherein the electromagnetic transducer is configured to produce pressure fluctuations in the fluid so as to eject fluid from the reservoir through the aperture.
28. The method according to Clause 27, wherein the electromagnetic transducer produces pressure fluctuations in the fluid by displacement induced on an external surface of the fluid package.
29. The method according to any of Clauses 26 to 28, wherein the electromagnetic transducer is configured to oscillate at an audible frequency.
30. The method according to Clause 29, wherein the audible frequency ranges from 50 to 5,000 Hz.
31. The method according to Clause 30, wherein the audible frequency ranges from 800 to 1200 Hz.
32. The method according to any of Clauses 26 to 31, wherein the electromagnetic transducer is configured to operate at an oscillation amplitude ranging from 2 to 3 μm.

33. The method according to any of Clauses 26 to 32, wherein the electromagnetic transducer comprises an electromagnet and a permanent magnet in operational proximity to each other.
34. The method according to Clause 33, wherein the permanent magnet is positioned at a first region of a cantilever beam.
35. The method according to Clause 34, wherein the electromagnetic transducer further comprises an anchor positioned at a second region of the cantilever beam and configured transmit oscillatory displacement force to an external surface of the drug package.
36. The method according to any of Clauses 26 to 35, wherein the electromagnetic transducer is reusable.
37. The method according to any of Clauses 26 to 36, wherein the fluid package comprises an expanded region comprising the reservoir and a neck region comprising the aperture.
38. The method according to any of the Clauses 26 to 37, wherein the aperture has a diameter ranging from 200 to 350 μm.
39. The method according to any of Clauses 26 to 38, wherein the reservoir is a multi-dose reservoir.
40. The method according to any of Clauses 26 to 39, wherein the fluid package is disposable.
41. The method according to any of Clauses 26 to 40, where the device is configured to eject fluid through the aperture as a stream having a velocity ranging from 50 to 150 m/s.
42. The method according to any of Clauses 26 to 41, further comprising an image-based alignment system configured to align fluid ejected through the aperture with a target ocular location.
43. The method according to Clause 42, wherein the image-based alignment system comprises a reflective surface.
44. The method according to any of Clauses 26 to 43, wherein the fluid package and electromagnetic transducer are present in a housing.
45. The method according to Clause 44, where the housing comprises a cover positioned along the housing, wherein the cover is configurable between an open position, in which the one or more apertures are exposed, and a closed position, in which the one or more apertures are not exposed.
46. The method according to Clause 45, wherein the cover comprises a sliding cover structure.
47. The method according to Clause 46, wherein the transducer is configured to be activated when the cover is in the open position.
48. The method according to Clause 47, wherein the electromagnetic transducer is configured to be deactivated when the cover is in the closed position.
49. The method according to any of Clauses 26 to 48, wherein the device comprises an illumination source.
50. The method according to any of Clauses 26 to 49, wherein the device further comprises a distance sensor configured to determine the distance between the device and a target location.
51. The method according to any of Clauses 26 to 50, wherein the target location is an ocular location.
52. The method according to Clause 51, wherein the ocular location comprises a corneal/conjunctival location.
53. The method according to Clause 52, wherein the ocular location comprises an area ranging from 2.5 to 12 μm².
54. The method according to any of Clauses 26 to 53, wherein the method is performed by the subject.
55. The method according to any of Clauses 26 to 54, wherein the method is a method of treating subject for an ocular condition.
56. A kit comprising a fluid delivery device according to any of Clauses 1 to 25 or a component thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A fluid delivery device, the device comprising:
   (a) a fluid package comprising:
      (i) a reservoir comprising an ophthalmic formulation; and
      (ii) an aperture through which the ophthalmic formulation can be directed, the aperture having a diameter ranging from 200 to 350 µm;
   (b) a pin member being in axial alignment with the aperture and engaging the reservoir; and
   (c) an electromagnetic actuator configured to axially oscillate the pin member while imparting pressure fluctuations to the fluid to eject fluid from the reservoir through the aperture at a velocity in a range from 10 to 500 cm/sec, which results in minimal discomfort during topical ocular delivery;
   wherein the electromagnetic actuator comprises an electromagnet and a permanent magnet in operational proximity to each other; and
   wherein the permanent magnet is positioned at a first region of a cantilever beam and the electromagnetic actuator further comprises an anchor positioned at a second region of the cantilever beam and configured to transmit oscillatory displacement force to an external surface of the fluid package.

2. The fluid delivery device according to claim 1, wherein the electromagnetic actuator imparts pressure fluctuations in the fluid by displacement induced on an external surface of the fluid package.

3. The fluid delivery device according to claim 1, wherein the electromagnetic actuator oscillates at an audible frequency in a range from 20 to 20,000 Hz.

4. The fluid delivery device according to claim 3, wherein the audible frequency ranges from 800 to 1200 Hz.

5. The fluid delivery device according to claim 1, wherein the electromagnetic actuator is configured to operate at an oscillation amplitude ranging from 2 to 3 µm.

6. The fluid delivery device according to claim 1, wherein the device is configured to eject fluid through the aperture as a stream having a velocity ranging from 50 to 150 cm/s.

7. The fluid delivery device according to claim 1, further comprising an image-based alignment system configured to align fluid ejected through the aperture with a target ocular location.

8. The fluid delivery device according to claim 1, wherein the fluid package and electromagnetic actuator are present in a housing.

9. The fluid delivery device according to claim 8, wherein the housing comprises a cover positioned along the housing, wherein the cover is configurable between an open position, in which the aperture is exposed, and a closed position, in which the aperture is not exposed.

10. A method of delivering a fluid to a topical ocular location of a subject, the method comprising:
    (a) aligning a fluid delivery device according to claim 1 with the topical ocular location; and
    (b) activating the electromagnetic actuator to eject fluid from the reservoir through the aperture to the topical ocular location at a velocity which results in minimal discomfort during topical ocular delivery.

11. A kit comprising a fluid delivery device according to claim 1.

12. A fluid delivery device, the device comprising:
    (a) a fluid package comprising:
       (i) a reservoir configured to hold a fluid; and
       (ii) an aperture through which the fluid can be directed;

(b) a pin member being in axial alignment with the aperture and engaging the reservoir; and (c) an electromagnetic actuator configured to axially oscillate the pin member while imparting pressure fluctuations to the fluid to eject the fluid from the reservoir through the aperture;

wherein the electromagnetic actuator comprises an electromagnet and a permanent magnet in operational proximity to each other; and wherein the permanent magnet is positioned at a first region of a cantilever beam and the electromagnetic actuator further comprises an anchor positioned at a second region of the cantilever beam and configured to transmit oscillatory displacement force to an external surface of the fluid package.

13. The fluid delivery device according to claim 12, wherein the fluid package and actuator are present in a housing.

14. The fluid delivery device according to claim 13, wherein the housing comprises a cover positioned along the housing, wherein the cover is configurable between an open position, in which the aperture is exposed, and a closed position, in which the aperture is not exposed.

15. The fluid delivery device according to claim 12, further comprising an image-based alignment system configured to align fluid ejected through the aperture with a target ocular location.

16. The fluid delivery device according to claim 15, where the image-based alignment system is a concave mirror.

* * * * *